United States Patent [19]
Breton et al.

[11] Patent Number: 5,902,805
[45] Date of Patent: *May 11, 1999

[54] METHOD FOR TREATMENT OF ACNE AND/OR THE EFFECTS OF AGEING USING HMG-COENZYME A-REDUCTASE INHIBITOR AND COMPOSITIONS FOR PERFORMING THE SAME

[75] Inventors: Lionel Breton, Versailles; Olivier De Lacharriere, Paris, both of France

[73] Assignee: L'Oreal, Paris, France

[ * ] Notice: This patent is subject to a terminal disclaimer.

[21] Appl. No.: 08/974,230

[22] Filed: Nov. 19, 1997

Related U.S. Application Data

[63] Continuation of application No. 08/635,577, Apr. 22, 1996, Pat. No. 5,733,558.

[51] Int. Cl.⁶ .......... A01N 37/36; A01N 43/00; A61K 31/60; A61K 31/62
[52] U.S. Cl. .......... 514/159; 514/161; 514/460; 514/844; 514/845; 514/847; 514/848; 514/852; 514/859; 514/861; 514/863; 514/887; 514/969; 424/401
[58] Field of Search .......... 424/401; 514/159, 514/161, 460, 844, 845, 847, 848, 852, 859, 861, 863, 887, 969

[56] References Cited

U.S. PATENT DOCUMENTS

| | | | |
|---|---|---|---|
| 4,767,750 | 8/1988 | Jacquet et al. | 514/159 |
| 5,021,451 | 6/1991 | McLane et al. | 514/460 |

OTHER PUBLICATIONS

Chemical Abstracts 76:103712, "Polyethylene glycols as Bases for Preparing Salicylic Adid Ointments", Miroslav et al., Oct. 1971.

*Primary Examiner*—Frederick Krass
*Attorney, Agent, or Firm*—Oblon, Spivak, McClelland, Maier & Neustadt, P.C.

[57] ABSTRACT

A method for the treatment of acne and/or the effects of ageing, by administering, to a subject in need thereof, a composition containing an effective amount of at least one HMG-Coenzyme A-reductase inhibitor in a carrier that is selected from the group consisting of dermatologically acceptable carriers, cosmetically acceptable carriers, and mixtures thereof, and the compositions for performing the method are provided.

17 Claims, No Drawings

METHOD FOR TREATMENT OF ACNE AND/OR THE EFFECTS OF AGEING USING HMG-COENZYME A-REDUCTASE INHIBITOR AND COMPOSITIONS FOR PERFORMING THE SAME

This is a continuation of application Ser. No. 08/635,577 filed on Apr. 22, 1996, now U.S. Pat. No. 5,733,558.

BACKGROUND OF THE INVENTION

FIELD OF THE INVENTION

The present invention relates to the use of an HMG-Coenzyme A-reductase inhibitor as an active anti-ageing agent, in or for the manufacture of a cosmetic and/or dermatological composition, its use in order to treat the effects of ageing and acne and to a topical composition containing the same in combination with an active agent possessing desquamating properties, acting in synergy.

DISCUSSION OF THE BACKGROUND

Ageing of the skin is the result of the effects of intrinsic and extrinsic factors on the skin. Clinically, the signs of ageing are reflected by the appearance of wrinkles and fine lines, by a slackening of cutaneous and subcutaneous tissue, by a loss of skin elasticity, by atonia of the skin texture and by yellowing of the skin, which becomes duller and lacking in radiance. On areas of skin which have been exposed to the sun throughout life—essentially the face, neckline, hands and forearms—pigmentation marks, telangiectasias and elastosis are often observed.

Some of these signs are more particularly associated with intrinsic or physiological ageing, (ageing associated with physical age), whereas others are more specific to extrinsic ageing, (ageing caused generally by the environment). Extrinsic ageing more particularly concerns photo-ageing due to exposure to the sun, to light or to any other radiation.

For several years now, cosmetic compositions have appeared on the market containing α-hydroxy acids, such as glycolic acid, malic acid and lactic acid, in order to combat the visible signs of ageing, in particular to combat wrinkles, fine lines, dull complexions and marks, as well as to remove comedones caused by acne. These compositions are generally in the form of creams or lotions.

In order to be active, these compositions must contain the α-hydroxy acid in its acid form (see in particular the article by W. P. Smith, Soap Cosmetic Chemical Specialities, September 1993, pp. 54–58 and 76: "Hydroxy acids and skin aging"), which gives the composition a low pH, leading to problems of skin tolerance. These skin tolerance problems take the form of stinging, redness and tightness which may lead to considerable discomfort.

Moreover, acne is essentially the consequence of two complex phenomena: the formation of a comedone and pericomedonian inflammation or folliculitis. The formation of a comedone itself is also the consequence of two phenomena: obstruction of the pilo-sebaceous duct and the increased production of sebum by the sebaceous glands, giving rise to the formation of blackheads. The acne is not inflammatory at the stage of formation of the comedone, but becomes so after the proliferation of bacteria resulting from seborrhoeic retention and the overproduction of sebum. The bacteria in question are, in particular, diphtheroid anaerobic bacteria such as Propionibacteria (acnes, granulosum, avidum). At the stage of formation of the comedone, the treatment may consist simply in cleaning the skin, whereas at the stage of inflammation, an anti-inflammatory treatment should be carried out.

Conventional acne treatments include keratolytic agents such as retinoids, particularly retinoic acid, anti-inflammatory agents such as peroxides, particularly benzoyl peroxide, and antiseborrhoeic agents. These active agents have the drawback of being fairly irritant. This irritant effect is experienced all the more so by an individual undergoing treatment who has sensitive skin.

Thus, there is a need for active agents having the same effect as α-hydroxy acids or as keratolytic agents without causing the above-noted problems of intolerance.

HMG-Coenzyme A-reductase inhibitors (β-hydroxy-β-methylglutaryl-Coenzyme A-reductase, referred to hereinbelow as HMG-CoA-reductase) are pharmaceutical active agents used orally in the treatment of hypercholesterolaemias (excessive levels of cholesterol in the plasma). (See in this respect "Pharmacologie, Des concepts fondamentaux aux applications therapeutiques [Pharmacology, From Fundamental Concepts to Therapeutic Applications]", published under the direction of M. Schorderet, Frison-Roche publishers, second edition, 1992).

These inhibitors are also used in the treatment of diseases linked to the excessive presence of cholesterol, such as arteriosclerosis.

HMG-CoA-reductase is an enzyme involved at a very early stage in the synthesis of cholesterol. In the epidermis, it is conventionally accepted that cholesterol and the metabolites thereof play an essential role in the cohesion of the epidermal cells and most particularly of the corneocytes (cells constituting the stratum corneum).

EP-A-369,263 describes the use of HMG-CoA-reductase inhibitors for the topical treatment of skin diseases, in particular keratosis and psoriasis. Moreover, E. Proksch et al describe that the topical application of HMG-CoA-reductase inhibitor disrupts the skin barrier function (see British Journal of Dermatology, 1993, Vol. 128, No. 5, p. 473–482), and M. Krasovec et al mention that the eczematous redness of certain patients treated with an HMG-CoA-reductase inhibitor may be due to a barrier dysfunction (see Dermatology, 1993, Vol. 186, No. 4, p. 248–252).

However, no document either describes or suggests the use of HMG-CoA-reductase inhibitors as active agents making it possible to attenuate, or even remove altogether, the signs of skin ageing. Furthermore, no document either describes or suggests the use of HMG-CoA-reductase inhibitors to treat acne.

SUMMARY OF THE PRESENT INVENTION

Accordingly, one object of the present invention is the use of at least one HMG-Coenzyme A-reductase inhibitor as an anti-ageing active agent in and/or for the manufacture of a cosmetic and/or dermatological composition.

Another object of the present invention is also the use of at least one HMG-Coenzyme A-reductase inhibitor in a cosmetic composition in order to combat wrinkles and/or fine lines and/or actinic marks and/or cutaneous dyschromias on human skin and/or to revive the radiance of human skin.

Another object of the present invention is the use of at least one HMG-Coenzyme A-reductase inhibitor for the manufacture of a dermatological composition in order to combat wrinkles and/or actinic marks and/or dyschromias and/or scars and/or ichthyosis of the human skin and/or acne.

Another object of the present invention is to provide a composition for treatment of the effects of ageing, comprising at least one HMG-Coenzyme A-reductase inhibitor and at least one additional active agent having desquamating properties.

These and other objects of the present invention have been satisfied by the discovery of

DETAILED DESCRIPTION OF THE PREFERRED EMBODIMENTS

The HMG-CoA-reductase inhibitors of the present invention include any compound which exhibits HMG-CoA-reductase inhibitory activity. Preferably, the HMG-CoA-reductase inhibitor is one of the following compounds: mevastatine, lovastatine, pravastatine, simvastatine, fluvastatine, dalvastatine, and the derivatives and salts thereof, most preferably the sodium salts thereof.

In the compositions according to the present invention, the HMG-CoA-reductase inhibitor (or a mixture of inhibitors) is used in an amount ranging from 0.000001 to 2% by weight relative to the total weight of the composition and preferably in an amount ranging from 0.00001 to 0.1% by weight relative to the total weight of the composition.

In the present composition, the HMG-CoA-reductase inhibitors may be combined with other active agents known for their desquamating property, such as hydroxy acids, α- or β-keto acids or retinoids. It has been observed, surprisingly, that such a combination makes it possible to decrease the active concentration of these products on account of the addition of their effects. A less irritant and less toxic composition, as well as a more effective composition, may thus be obtained.

Thus, in a further embodiment of the present invention a cosmetic composition is provided containing, in a cosmetically acceptable medium, at least one HMG-Coenzyme A-reductase inhibitor and at least one active agent possessing desquamating properties, wherein the inhibitor and desquamating agent act in synergy with one another.

Suitable hydroxy acids include α-hydroxy acids or β-hydroxy acids, which may be linear, branched or cyclic and saturated or unsaturated. The hydrogen atoms of the carbon chain may, moreover, be substituted one or more times with halogen, alkyl, acyl, acyloxy, alkoxycarbonyl or alkoxy radicals having from 2 to 18 carbon atoms.

Preferred hydroxy acids include glycolic acid, lactic acid, malic acid, tartaric acid, citric acid and fruit acids in general, 2-hydroxyalkanoic acids, mandelic acid, salicylic acid, as well as alkyl derivatives thereof, such as 5-n-octanoylsalicylic acid, 5-n-dodecanoylsalicylic acid, 5-n-decanoylsalicylic acid, 5-n-octylsalicylic acid, 5- or 4-n-heptyloxysalicylic acid, 2-hydroxy-3-methylbenzoic acid or alternatively alkoxy derivatives thereof such as 2-hydroxy-3-methoxybenzoic acid. The hydroxy acids may be in free or salified form, preferably in the form of salts obtained by salification with an inorganic or organic base.

Suitable retinoids include retinoic acid (all-trans or 13-cis) and derivatives thereof, retinol (vitamin A) and esters thereof, such as retinyl palmitate, retinyl acetate and retinyl propionate, as well as salts thereof.

By way of example, the hydroxy acids, the keto acids and the retinoids may be used in the compositions according to the present invention in an amount representing 0.1 to 10 and preferably from 0.1 to 5% by weight of the total weight of the composition, and more preferably from 0.5 to 3% by weight. (Note: all % are weight % unless otherwise indicated).

Using the compositions of the present invention, desquamation of the skin, consisting of removing the surface cells of the skin, leads to a smoothing out of the lines, a revival of the complexion, a reduction of wrinkles and fine lines as well as a decrease, or even a removal, of actinic marks and/or of dyschromias on the skin.

In a further embodiment of the present invention a cosmetic and/or dermatological treatment process is provided for treating wrinkles and/or fine lines on human skin and/or for reviving the radiance of human skin and/or for treating acne, which consists in applying to the skin an effective amount of a composition containing at least one HMG-Coenzyme A-reductase inhibitor in a suitable dermatologically acceptable carrier.

The subject of the invention is also a process for the cosmetic or dermatological treatment of the skin intended for the desquamation of the skin, which consists in applying to the skin a composition containing at least one HMG-Coenzyme A-reductase inhibitor.

The subject of the invention is also a process for the cosmetic or dermatological treatment of ageing of the skin, which consists in applying to the skin a composition containing at least one HMG-Coenzyme A-reductase inhibitor.

The composition of the present invention contains a cosmetically or dermatologically acceptable carrier. Such a carrier is a medium which is compatible with the skin, the nails, the mucous membranes, tissues and the hair and includes any conventionally used cosmetic or dermatological carrier which meets these requirements. Such carriers can be readily selected by one of ordinary skill in the art.

The present composition containing the HMG-CoA-reductase inhibitor may be applied topically to the face, the neck and the mucous membranes or any other region of body skin.

The compositions according to the present invention may be in any form suitable for topical application, preferably in the form of aqueous, aqueous-alcoholic or oily solutions, dispersions of the lotion or serum type, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions are prepared according to conventional methods.

The present compositions may optionally be in the form of aerosol compositions also containing a conventional cosmetically or dermatologically acceptable propellant under pressure.

Other than the HMG-CoA-reductase inhibitor, the amounts of the various constituents of the compositions according to the invention are those conventionally used in the art.

These compositions in particular constitute protection, treatment or care creams, milks, lotions, gels or foams for the face, for the hands, for the body and/or for the mucous membranes, or for cleansing the skin.

The compositions may also consist of solid preparations constituting soaps or cleansing bars.

When the composition of the present invention is an emulsion, the proportion of the fatty phase may range from 5% to 80% by weight, and preferably from 5% to 50% by weight, relative to the total weight of the composition. The oils, emulsifying agents and co-emulsifying agents used in the composition in emulsion form are chosen from those conventionally used in the cosmetic or dermatological field.

The emulsifying agent and the co-emulsifying agent are present in the present composition in a proportion ranging from 0.3% to 30% by weight, and preferably from 0.5 to 20% by weight, relative to the total weight of the composition. The emulsion may also contain lipid vesicles.

When the present composition is an oily gel or solution, the amount of oil may range up to more than 90% by weight of the total weight of the composition.

The composition of the present invention may also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from 0.01% to 20% of the total weight of the composition. Depending on their nature, these adjuvants may be introduced into the fatty phase, into the aqueous phase and/or into the lipid vesicles.

Suitable oils which may be used in the present invention, include mineral oils (liquid petrolatum), plant oils (karite butter and sweet almond oil), animal oils, synthetic oils, silicone oils (cyclomethicone) and fluoro oils (perfluoropolyethers). Fatty alcohols, fatty acids (stearic acid) and waxes (paraffin wax, carnauba wax or beeswax) may also be used as fatty substances.

Suitable emulsifying agents for the compositions of the present invention include Polysorbate 60 and sorbitan stearate which are sold respectively under the trade names Tween 60 and Span 60 by ICI. Co-emulsifying agents such as PPG-3 myristyl ether sold under the trade name Emcol 249-3K by Witco may be added thereto.

Suitable solvents which may be used in the present invention, include lower alcohols, in particular ethanol and isopropanol, and glycols such as propylene glycol. (Note: use of the term "lower" herein refers to $C_1$–$C_4$ compounds unless otherwise specified).

Hydrophilic gelling agents which may be used include carboxyvinyl polymers (carbomer), acrylic copolymers such as acrylate/alkylacrylate copolymers, polyglyceryl (meth) acrylates such as the product sold under the name Norgel by Guardian, polyacrylamides and in particular the mixture of polyacrylamide, C13-14-isoparaffin and Laureth-7, sold under the name Sepigel 305 by Seppic, polysaccharides such as hydroxypropylcellulose, natural gums (xanthan) and clays. Lipophilic gelling agents which may be used include modified clays such as bentones, fatty acid metal salts such as aluminium stearates, hydrophobic silica, polyethylenes and ethylcellulose.

Hydrophilic active agents which may be used include proteins or protein hydrolysates, amino acids, polyols, ureas, allantoin, sugars and sugar derivatives, water-soluble vitamins, starch and bacterial or plant extracts, in particular Aloe vera.

Lipophilic active agents which may be used include tocopherol (vitamin E) and derivatives thereof, essential fatty acids, ceramides and essential oils.

The HMG-CoA-reductase inhibitors may be combined, inter alia, with active agents intended in particular for the prevention and/or treatment of skin complaints. Among these active agents which may be mentioned are, for example:

agents which modify the differentiation and/or proliferation and/or pigmentation of the skin, such as vitamin D and derivatives thereof, estrogens such as estradiol, kojic acid or hydroquinone;

antibacterial agents such as clindamycin phosphate, erythromycin or antibiotics of the tetracycline family;

antifungal agents, preferably compounds belonging to the imidazole family such as econazole, ketoconazole or miconazole or salts thereof, polyene compounds such as amphotericin B, compounds of the allylamine family such as terbinafine, or alternatively octopirox;

steroidal anti-inflammatory agents, such as hydrocortisone, anthralins (dioxyanthranol), anthranoids, betamethasone valerate or clobetasol propionate;

anti-free-radical agents, such as alpha-tocopherol or esters thereof, superoxide dismutases, certain metal-chelating agents or ascorbic acid and esters thereof;

antiseborrhoeic agents such as progestone;

antiacne agents such as retinoic acid or benzoyl peroxide; and antiseptics.

The treatment process of the present invention may be carried out in particular by applying the cosmetic, hygienic or dermatological compositions as defined above, according to the usual technique for the use of these compositions. For example: application of creams, gels, sera, lotions or milks to the skin, the scalp and/or the mucous membranes.

Having generally described this invention, a further understanding can be obtained by reference to certain specific examples which are provided herein for purposes of illustration only and are not intended to be limiting unless otherwise specified.

EXAMPLES

The effectiveness of HMG-Coenzyme A-reductase inhibitors of the present invention on the treatment of the signs of ageing was determined by carrying out an in vitro desquamation test.

This in vitro test was performed on keratinocytes using 5-n-octanoylsalicylic acid, mevastatine and a mixture of the two. The principle of the test was based on the fact that desquamation induces the release of corneocytes. Thus, the desquamating power of the test product is greater the larger the number of corneocytes released.

The test procedure was as follows: keratinocytes were obtained from skin biopsies by separation of the epidermis and were dissociated by enzymatic action with trypsin and cultured at a concentration of $2\times10^{-5}$ cells/ml. The growth and differentiation of the keratinocytes was obtained by culturing for 10 to 20 days in a specific medium.

Next, after removal of the culture medium, the test product was added and the activity of the product evaluated. To do this, two samples were taken at T=0 and T=60, that is to say, before the addition of the product and 60 minutes after this addition, and the obtained samples were analysed on a flow cytometer in order to count the population of corneocytes. The populations of corneocytes and keratinocytes were differentiated on the flow cytometer by treatment with acridine orange specific for cellular DNA, which attaches to the cell nucleus and thus reveals only the presence of the keratinocytes.

The cellular detachment number was determined by the difference between T=60 and T=0.

The same measurement was taken for a control containing no test product, since the experiment inevitably produces the release of corneocytes, even in the absence of active agent. The variation of the control arbitrarily set the standard of 100%.

The results are presented in the table below

| Control | Mevastatine (Compound I) $5\cdot10^{-7}$ M | 5-n-Octanoyl-salicylic acid (Compound II) $5\cdot10^{-5}$ M | (Compound I at $5\cdot10^{-7}$ M) + (Compound II at $5\cdot10^{-5}$ M) |
|---|---|---|---|
| 100% | 299.5% | 219% | 393% |

These results show that mevastatine, at a concentration 100 times lower than the 5-n-octanoylsalicylic acid, is much more active than the latter, and that the mixture of the two does not lead to a saturation of the desquamation effect but, on the contrary, to an addition of the effects of each of these compounds. This additive effect shows that the desquamation processes of mevastatine and of 5-n-octanoylsalicylic acid are different. This results in an additive effect of the desquamating active agent (5-n-octanoylsalicylic acid) and of the HMG-Coenzyme A-reductase inhibitor.

In the following examples, the proportions indicated are percentages by weight.

| Example 1: O/W emulsion | |
|---|---|
| Phase A: | |
| 5-n-Octanoylsalicylic acid | 0.5 |
| Mevastatine | 0.001 |
| Sweet almond oil | 14.5 |
| Karite butter | 7.0 |
| PPG-3 myristyl ether (EMCOL 249-3K) | 5.0 |
| Preserving agent (propyl paraben) | 0.1 |
| Polysorbate 60 (Tween 60) | 2.5 |
| Sorbitan stearate (Span 60) | 2.5 |
| Phase B: | |
| Cyclomethicone | 4.0 |
| Xanthan gum | 0.2 |
| Carboxyvinyl polymer | 0.5 |
| Phase C: | |
| Triethanolamine (neutralizing agent) | 0.5 |
| Water | 2.0 |
| Phase D: | |
| Preserving agent (methyl paraben) | 0.2 |
| Glycerol | 5.0 |
| Water | qs 100 |

Procedure:

The constituents of phase A were melted at 85° C. and phase A was then cooled to 70° C. and the phases B and then C and D were introduced therein with stirring. The mixture was cooled to room temperature.

A day cream was obtained which, after applying for several days, made the skin look smoother and younger than before the treatment and reduced marks.

| Example 2: Gel | |
|---|---|
| Fluvastatine (sodium salt) | 0.005 |
| Hydroxypropylcellulose (Klucel H sold by the company Hercules) | 1.0 |
| Antioxidant | 0.05 |
| Isopropanol | 40.0 |
| Preserving agent | 0.3 |
| Water | qs 100 |

A gel was obtained which, on regular application, made it possible to fade out marks on the skin.

| Example 3: Solution for dermatological application | |
|---|---|
| Mevastatine | 0.05 |
| Antioxidant | 0.05 |
| Ethyl alcohol | 10 |
| Preserving agent | 0.3 |
| Water | qs 100 |

The application of this solution under dermatological control made it possible to obtain a fading out of marks and dyschromias, a smoothing out of wrinkles and fine lines and an improvement in the clinical state of the skin, the appearance of which became that of a younger skin.

This application was made one to three times a week for 4 to 6 weeks.

| Example 4: Gel for treating acne | |
|---|---|
| Polyglyceryl acrylate (Norgel) | 29.5% |
| Polyacrylamide/C13–14 isoparaffin/Laureth-7 (Sepigel 305) | 2% |
| Silicone oil | 10% |
| Lovastatine | 0.05% |
| Sodium salt of EDTA (sequestering agent) | 0.1% |
| Preserving agent | 0.4% |
| Water | qs 100% |

On daily application, the gel obtained was suitable for the treatment of acne.

What is claimed as new and desired to be secured by Letters Patent of the United States is:

1. A method for treating the effects of skin ageing by desquamation of skin cells, comprising desquamating skin cells by administering, to a subject in need thereof, a composition comprising an effective amount of at least one HMG-coenzyme A-reductase inhibitor in a carrier that is selected from the group consisting of dermatologically acceptable carriers, cosmetically acceptable carriers, and mixtures thereof.

2. The method of claim 1, wherein the at least one HMG-CoA-reductase inhibitor is in a cosmetically acceptable carrier and is present in an amount effective to combat wrinkles, fine lines, actinic marks, cutaneous dyschromias on human skin, to revive the radiance of the skin or a combination thereof.

3. The method of claim 1, wherein the at least one HMG-CoA-reductase inhibitor is in a dermatologically acceptable carrier and is present in an amount effective to combat wrinkles, actinic marks, cutaneous dyschromias, scars, ichthyosis, acne or a combination thereof.

4. The method of claim 1, wherein the HMG-CoA-reductase inhibitor is selected from the group consisting of mevastatine, lovastatine, pravastatine, simvastatine, fluvastatine, dalvastatine, and mixtures thereof.

5. The method of claim 1, wherein the HMG-CoA-reductase inhibitor is present in an amount ranging from 0.000001 to 2% by weight relative to the total weight of the composition.

6. The method of claim 1, wherein the composition further comprises at least one additional active desquamation agent.

7. The method of claim 6, wherein the at least one additional active desquamation agent is selected from the group consisting of α-hydroxy acids, β-hydroxy acids, α-keto acids, β-keto acids, retinoids and combinations thereof.

8. The method of claim 7, wherein the at least one additional active desquamation agent is a member selected from the group consisting of glycolic acid, lactic acid, malic acid, tartaric acid, citric acid, 2-hydroxyalkanoic acid, mandelic acid, salicylic acid and 5-n-octanoylsalicylic acid.

9. The method of claim 6, wherein the at least one additional active agent is present in an amount ranging from 0.1 to 5% by weight relative to the total weight of the composition.

10. The method of claim 1, wherein the composition further comprises at least one adjuvant selected from the group consisting of proteins, protein hydrolysates, amino acids, polyols, urea, sugars and sugar derivatives, vitamins, starches, plant extracts, essential fatty acids, ceramides and essential oils.

11. The method of claim 1, wherein the composition is in the form of an aqueous, oily or aqueous-alcoholic solution, a water-in-oil emulsion, an oil-in-water emulsion, a microemulsion, an aqueous gel, an anhydrous gel, a serum or a dispersion of vesicles, microcapsules or microparticles.

12. A cosmetic composition, comprising at least one HMG-Coenzyme A-reductase inhibitor and at least one additional active desquamation agent selected from the group consisting of $C_8$–$C_{12}$-alkanoyl salicylic acids in a cosmetically acceptable carrier.

13. The cosmetic composition according to claim 12, wherein the HMG-Coenzyme A-reductase inhibitor is selected from the group consisting of mevastatine, lovastatine, pravastatine, simvastatine, fluvastatine, dalvastatine, and mixtures thereof.

14. The cosmetic composition of claim 12, wherein the cosmetically acceptable carrier is selected to provide a composition in a form selected from the group consisting of an aqueous, oily solution, an aqueous-alcoholic solution, a water-in-oil emulsion, an oil-in-water emulsion, a microemulsion, an aqueous gel, an anhydrous gel, an oily gel, a serum and a vesicle dispersion.

15. The cosmetic composition according to claim 12, wherein the HMG-Coenzyme A-reductase inhibitor is present in an amount ranging from 0.000001 to 2% by weight relative to the total weight of the composition.

16. The cosmetic composition according to claim 12, further comprising one or more cosmetically acceptable adjuvants selected from the group consisting of hydrophilic gelling agents, lipophilic gelling agents, hydrophilic active agents, lipophilic active agents, preserving agents, antioxidants, solvents, fragrances, fillers, sunscreens, odor-absorbers and dyestuffs.

17. The cosmetic composition according to claim 12, wherein the cosmetically acceptable carrier is selected so as to provide a composition in a form selected from the group consisting of creams, milks, lotions, gels, foams, soaps and aerosols.

* * * * *

UNITED STATES PATENT AND TRADEMARK OFFICE
CERTIFICATE OF CORRECTION

PATENT NO. : 5,902,805

DATED : May 11, 1999

INVENTOR(S): Lionel BRETON, et al.

It is certified that an error appears in the above-identified patent and that said Letters Patent is hereby corrected as shown below:

On the title page, item [30] Foreign Application Priority Data has been omitted. It should be:

--[30]   Foreign Application Priority Data
   Apr. 20, 1995 [FR] France ............... 95-04747--

Signed and Sealed this

Eleventh Day of April, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO. : 5,902,805

DATED : May 11, 1999

INVENTOR(S): Lionel BRETON, ET AL.

It is certified that an error appears in the above-identified patent and that said Letters Patent is hereby corrected as shown below:

Column 3, lines 7-8, "These and other objects of the present invention, have been satisfied by the discovery of" should read --These and other objects are provided by the present invention.--.

Signed and Sealed this

Twelfth Day of December, 2000

Attest:

Q. TODD DICKINSON

*Attesting Officer*     *Director of Patents and Trademarks*